United States Patent [19]
Friemel et al.

[11] Patent Number: 5,655,535
[45] Date of Patent: Aug. 12, 1997

[54] 3-DIMENSIONAL COMPOUND ULTRASOUND FIELD OF VIEW

[75] Inventors: Barry H. Friemel, Issaquah; Lee Weng, Bellevue; Tat-Jin Teo, Redmond, all of Wash.

[73] Assignee: Siemens Medical Systems, Inc., Iselin, N.J.

[21] Appl. No.: 622,904

[22] Filed: Mar. 29, 1996

[51] Int. Cl.⁶ ........................................ A61B 8/00
[52] U.S. Cl. ................. 128/660.07; 128/660.08; 128/916
[58] Field of Search ............ 128/660.07, 661.09, 128/660.01, 660.08, 916

[56] References Cited

U.S. PATENT DOCUMENTS 5,159,931  11/1992  Pini ..................... 128/660.07

Primary Examiner—Francis Jaworski
Assistant Examiner—Derrick Fields

[57] ABSTRACT

A compounded field of view ultrasound image is derived from correlated frames of ultrasound image data. An operator manually translates an ultrasound probe across a patient target area. Frames of sensed echo signals are processed to detect probe motion without the use of a dedicated position sensor or motion sensor. Motion is detected by correlating the frames for probe translation among as many as 6 degrees of freedom. Image registration then is performed for correlated portions to compound a large ultrasound image. Such image encompasses an area larger than a single field of view image frame for the given manually-scanned transducer probe.

14 Claims, 2 Drawing Sheets

3-DIMENSIONAL COMPOUND ULTRASOUND FIELD OF VIEW

CROSS REFERENCE TO RELATED APPLICATIONS

This invention is related to U.S. patent application Ser. No. 08/414,978 filed Mar. 31, 1995, now U.S. Pat. No. 5,557,286, of Lee Weng and Arun P. Tirumalai for Method and Apparatus for Generating Large Compound Ultrasound Image. The content of that application is incorporated herein by reference and made a part hereof.

BACKGROUND OF THE INVENTION

This invention relates to medical diagnostic ultrasound imaging, and more particularly to a method and apparatus for compounding ultrasound fields of view to acquire large ultrasound images.

Medical diagnostic ultrasound systems are commonly used to generate two-dimensional diagnostic images of internal features within a patient's body. To do so, a sonographer positions an ultrasound transducer probe adjacent to a patient's target area. The probe is a non-intrusive device including an array of acoustic transducer elements. The transducer elements emit ultrasonic energy at a frequency on the order of 2.0 MHz to 10 MHz. The transmitted ultrasound energy propagates into the patient whom it is in part absorbed, dispersed, refracted, and reflected by internal structures. Reflected ultrasound energy is received back at the transducer probe where it is converted back into electronic signals. Body tissues, for example, appear as discontinuities or impedance changes in the converted electronic signals.

Converted electronic signal samples undergo beamforming to correlate the samples in time and space to a patient's target area. Exemplary beamforming parameters for controlling the imaging process include focus, steering, apodization and aperture. Focus is a time delay profile of active transducer elements. Steering is the control of focus depth points along azimuth and elevation axes of a transducer probe scan. Apodization is a voltage weighting profile of active transducer elements. Aperture is the control of the number of transducer elements which am active along azimuth or elevation axes of the transducer probe for a given scan. The beamformed data are processed to analyze echo, doppler, and flow information and obtain a cross-sectional image of the patient's targeted anatomy (e.g., tissue, flow, doppler).

A conventional image is a brightness image (i.e., referred to as a 'B-mode image') in which component pixels are brightened in proportion to a corresponding echo sample strength. The B-mode image represents a cross section of the patient target area through a transducer's scanning plane. Typically the B-mode image is a gray scale image in which the range of lighter to darker gray-scale shades correspond to increasing brightness or echo strength. The typical ultrasound B-mode image is formed by a linear scan or sector scan of the patient's target area by the transducer probe. The individual images produced by ultrasound imaging systems include discrete frames. For a given scanning frame in which first active transducer elements transmit an ultrasound signal and second active transducer elements receive an ultrasound echo, the transducer probe defines a given field of view. Such field of view depends on the number of active transducer elements, the relative spacing of the elements and the steering and focus of each element. Each frame has a limited field of view due to a relatively narrow region traversed by the transmitted ultrasound energy. As the transducer probe is manipulated along the patient's body surface, each previous image is replaced off the viewing display by a new image defined by the current position, and thus field of view, of the transducer probe.

Given the generally narrow field of view of conventional ultrasound systems, it is desirable to extend the field of view to acquire images over large portions of the patient anatomy. Increasing the number of transducers is one approach. However, such approach adds significant hardware expense and processing overhead cost. Another approach is to compound images from the scanning process into a larger image. Previously, it has been demonstrated that a real-time compound ultrasound two-dimensional image could be generated by using so-called compound B-scanners. These B-scanners use a transducer mounted on an arm assembly that constrains the transducer to move along a single plane or axis. Either the arm assembly or the transducer element itself is provided with sensing devices for tracking the precise position of the transducer. This positional information then is used to register each one of discrete image frames into a composite image. An example of an arm assembly is disclosed in U.S. Pat. No. 4,431,007 to Amazeen et al. for Referenced Real-Time Ultrasound Image Display.

Systems and methods relying on hardware position sensors have several shortcomings for expanding the field of view. First, popular position sensors are based on electromagnetic energy emissions. An electromagnetic sensor, however, is to be avoided in an ultrasound system because the electromagnetic energy interferes with the transmitted and received ultrasound energy. Other hardware position sensors tend to be less accurate requiring longer and more frequent calibration processes. Also, it is a challenge to integrate the sensor's detection scheme into the ultrasound image capturing process. The position sensor captures data samples. Such samples need to be synchronized to the ultrasound sampling process and the ultrasound data processing data.

The hardware position sensor typically is located on the transducer probe. Thus the design of the probe (e.g., size and shape) is affected. This poses an ergonomic challenge in appeasing the sonographer. Sonographers tend to prefer limiting the gadgetry included on the probe. Accordingly, there is a need for expanding the ultrasound probe field of view without the use of a hardware position sensor. Specifically, for any given transducer array size, it is desirable to implement a method for expanding or compounding the field of view. Such method should be compatible with modern hand-held ultrasound transducers without encumbering the hand-held transducers with position sensing devices that increase the cost, weight and complexity of such imaging systems.

SUMMARY OF THE INVENTION

According to the invention, a compounded 3-D field of view ultrasound image is acquired by manually translating an ultrasound probe across a patient target area, detecting the motion without a dedicated position sensor, then deriving and displaying a compound image. Motion is detected by correlating frames of ultrasound data for translation within various degrees of freedom. Image registration is performed to compound a large ultrasound image. Such image encompasses an area larger than a single field of view image frame for the given manually-scanned transducer probe.

According to one aspect of the invention, frames of ultrasound data are processed to identify transducer motion within six degrees of freedom. The transducer emits ultrasound energy into the patient. The scan plane defined by the unobstructed path of such energy is used herein as a reference plane for naming the various degrees of freedom. Translation within the scan plane of the transmitted ultrasound is referred to as being "in-plane". Movement of the transducer in-plane along an azimuthal (e.g., 'x') axis is referred to as lateral translation, or in-plane lateral translation. Movement of the transducer in-plane inward toward the patient (e.g., along an y axis) is referred to as axial translation, or in-plane axial translation. Rotating the transducer (at an angle θ) within the plane about a normal axis z, as if adjusting the beam steering, is referred to as in-plane rotation. Movement of the transducer to move the scan plane parallel to its prior position (e.g., along a 'z' axis) is referred to as elevational translation. Movement of the transducer to rotate the scan plane (at an angle α) about the 'x' axis is referred to as axial rotation. Movement of the transducer to rotate the plane (at an angle φ) about the 'y' axis is referred to as rotation about the transducer face.

According to another aspect of the invention, the method for generating an ultrasound image of a patient target area encompassing a field of view extended beyond a given transducer array's field of view, includes the steps of: moving the transducer array within any of six degrees of freedom while the transducer array is positioned at a patient in the vicinity of the target area. The transducer array emits ultrasound signals and receives returning echoes of the emitted ultrasound signals. At another step, the received echoes within a scan plane are sampled to generate a plurality of frames of echo data for respective positions of the transducer array relative to the patient. A given frame of echo data encompasses a field of view of a first size. The plurality of flames of echo data are correlated to derive at least one in-plane motion vector for each one of multiple frames of the plurality of frames. Data rotation is performed on the multiple frames to derive corresponding multiple intermediate frames in which in-plane motion variation is factored out. The multiple intermediate frames then are correlated to derive at least one out-of-plane motion vector component for each one of the multiple intermediate frames. The correlated portions of the multiple intermediate frames are aggregated using the in-plane motion vectors and the out-of-plane motion vector components to define a 3-dimensional image encompassing a field of view of a second size. The second size is larger than the first size. The multiple intermediate frames are correlated to derive at least one out-of-plane motion vector component for each one of the multiple intermediate frames by using time delays, spectral breadth, power or speckle decorrelation as an indicator of elevational motion.

According to another aspect of the invention, elevational translation is estimated by measuring time delays among signals in the near field of the transducer scan plane. The received signal from each transducer element in a given column along the elevation at a fixed depth over time is referred to as $s(x,y_0,z_n,t)$. As the transducer array moves along the elevation, ultrasound scatterers pass into the scan-plane of a transducer element $z_0$ at a time $t_0$ and beneath an element $z_1$ at a time $t_1$. The measure of the time delay between the signals from each of the two elements, (i.e., $z_0$ and $z_1$) is directly proportional to transducer velocity. One-dimensional cross-correlation is performed on the received signals over time from the near field at adjacent or nearby transducer elements to define the elevational motion vector component.

According to another aspect of the invention, elevational translation is estimated alternatively by measuring spectral breadth of a pulsed-wave doppler spectrum for each transducer element. As a given transducer element is translated in the elevation direction (i.e., along the z axis) a single sample is taken periodically at a given range. The sampling rate is defined by a pulse repetition frequency. Each sample is transformed from the time domain into the frequency domain using a fast Fourier transform ('FFT') or the like. The resulting frequency domain representation of multiple samples from the same element is its pulsed-wave doppler spectrum. As the spectrum is expected to be triangular, one measure for determining breadth of the spectrum is to fit a triangle to the intermediate frame data, then determine the zero crossovers. The frequency band between zero crossovers is a measure of spectral breadth. Alternatively, a 3 dB width or 6 dB width measurement of the spectrum is used as the measure of spectral breadth.

According to another aspect of the invention, elevational translation is estimated alternatively by measuring the power function of the echo signal at each given transducer element. The power function is approximately equal to the integral of the pulsed-wave doppler spectrum for the given transducer element. The power function of the doppler signal is proportional to elevational velocity. To determine the power function the echo data for a given transducer is applied to a low-pass wall filter. A broader spectrum output from the wall filter correlates to more energy in the pass band of the filter. The amount of energy correlates directly to the velocity of the transducer. Because axial and lateral translation also appears as increased energy in the pass band, the effects of axial and lateral translation are first factored out before estimated elevational translation using the power mode.

According to another aspect of the invention, elevational translation is estimated alternatively by measuring speckle decorrelation among successive frames. As the transducer is moved in the elevational direction, the ultrasonic speckle changes due to changes of the anatomical structure in the scan plane. The elevational velocity is estimated by examining the rate of speckle decorrelation in the echo response data. More specifically, elevational motion is estimated by examining the rate of speckle decorrelation in the echo response data after in-plane motion is factored out.

According to another aspect of the invention, elevational motion vectors for multiple transducer elements are used to derive other out-of-plane motion vector components. Axial rotation is estimated using multiple elevational translation estimates. In one embodiment two estimates of elevational translation are determined at either end of a row of transducer elements (i.e., along the azimuthal x axis). Estimates at different depths then equate to an estimate for axial rotation. Similarly rotation about the face of the transducer is estimated using two estimates of elevational translation taken at either end of a given column of transducer elements (i.e., along the elevational z axis). Estimates at different depths then equate to an estimate for rotation about the face of the transducer.

According to one advantage of the invention, expanding the field of view enables the generation of compounded 3-dimensional (3D) ultrasound images. By correlating data from various frames to detect various translational and rotational movements of the probe, a dedicated hardware position sensor or a dedicated hardware motion sensor is avoided. As a result, the transducer probe need not be altered to accommodate the additional sensor. These and other aspects and advantages of the invention will be better understood by reference to the following detailed description taken in conjunction with the accompanying drawings.

DESCRIPTION OF SPECIFIC EMBODIMENTS

Exemplary Ultrasound Host Platform

Figure 1:
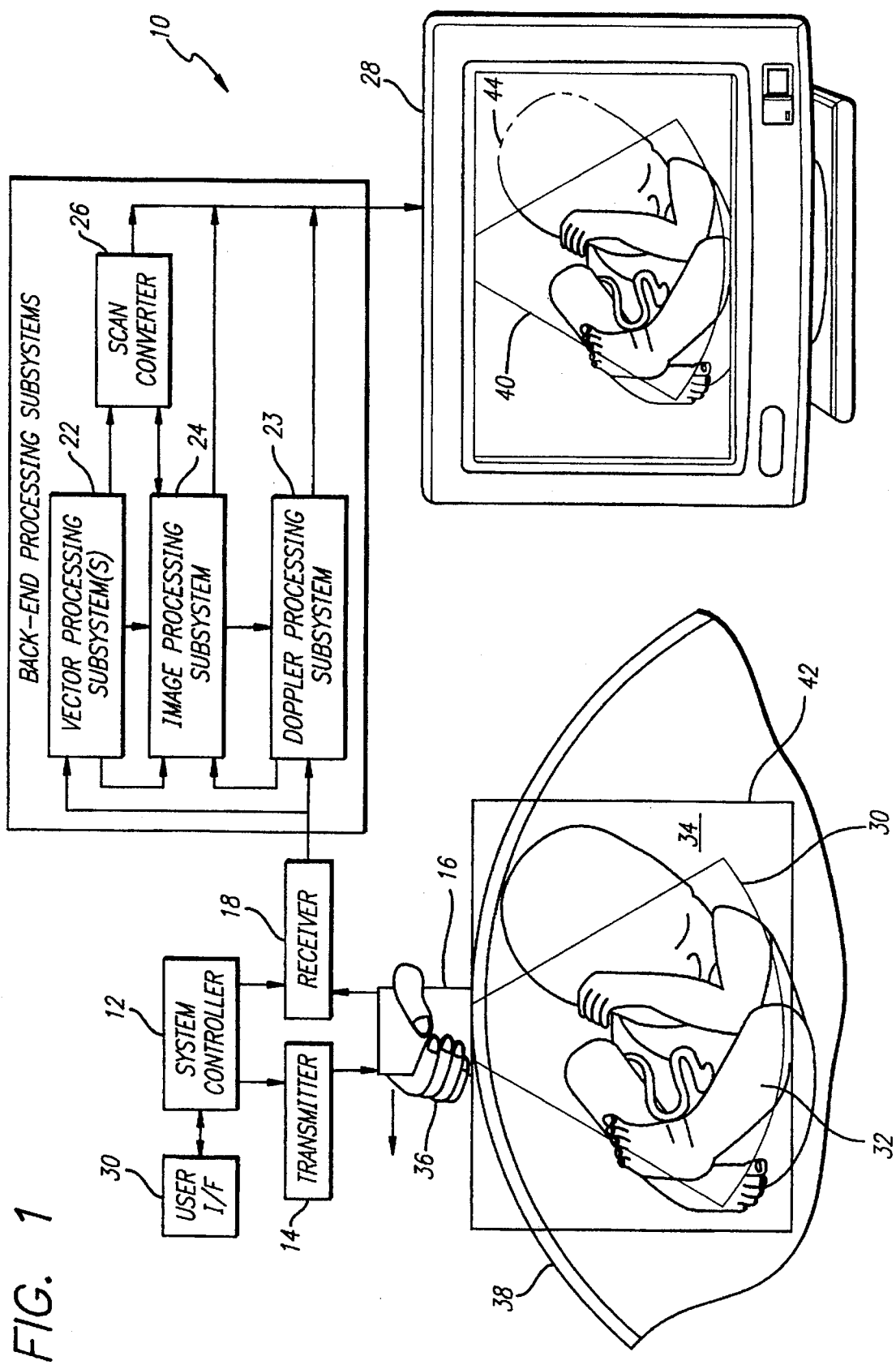
FIG. 1 is a block diagram of an ultrasound imaging system embodiment for implementing the method of this invention.

FIG. 1 shows an ultrasound medical diagnostic imaging system 10. The system 10 emits ultrasound signals and detects response echoes to scan a target area within a patient's anatomy. The ultrasound system 10 includes a system controller 12, transmitter 14, transducer 16, receiver 18, vector processing subsystem(s) 22, doppler processing subsystem 23, image processing subsystem 24, scan converter 26 and display 28. The system controller 12 provides a user interface 30 (e.g., .control panel, display menu, keyboard) and controls system operations. In operation, the system controller 12 triggers the transmitter 14 to generate electrical signals for output to the transducer 16. The transducer 16 converts the electrical signals into an ultrasound transmit wave-pattern. Typically, the transducer 16 is positioned adjacent to and in contact with a patient's anatomy. The transmit wave-pattern propagates into the patient's anatomy where it is refracted, absorbed, dispersed and reflected. The degree of refraction, absorption, dispersion and reflection depends on the uniformity, density and structure of the encountered anatomy. Of interest is the reflected components which propagate back to the transducer 16. These echoes are sensed by the transducer 16 and converted back into electrical signals. The electrical signals are input to a receiver 18 which amplifies the signals. A beamformer portion of receiver 18 groups the echo signals into correlated frames of data scans for given target areas.

A common ultrasound diagnostic application is for examining a fetus 32 within a mother's womb 34. A sonographer 36 moves the transducer 16 along the patient's skin surface 38 in a direction parallel with the ultrasonic scan plane 40. An acoustically conductive lubricating agent typically is applied to the skin prior to the examination to improve acoustic coupling between the transducer 16 and the patient's skin 38. The transmitter 14 sends electrical signals to the transducer 16 causing ultrasound pulses to be emitted into the patient. The pulses propagate through the patient's skin into the body. The pulses in part echo off the fetus 32 returning through the skin 38 to the transducer 16. The transducer 16 converts the echo pulses back into electrical signals. After beamforming, raw beamformed data is fed to back-end processing subsystems 22–26. The back-end processing subsystems typically perform echo processing, doppler processing, color flow processing, image processing, scan conversion and video processing. Conventional image processing of raw beam-formed echo data includes generating gray-scale image data corresponding to a patient's target area. Typically, raw data is encoded by applying a gray-scale value proportional to the echo intensity for a given vector sample. Scan conversion is performed to fill in values for pixels between vector samples. For some applications the encoded image data also is electronically stored in a memory medium, such as a permanent memory storage device (e.g., disk or tape) or a temporary storage device (e.g., solid state memory). Also, the encoded image data often is printed out in a hard copy format, such as a photograph.

In conventional applications, the image displayed on display 28 includes only the information representative of a relatively narrow region defined by the scan plane 40 at a given moment in time. Thus, only a portion of the anatomical features of the fetus 32 are displayed at a given time. According to the method of this invention, however, the display image is compounded from multiple frames to derive a larger 2D or 3D compounded field of view 42 ultrasound image 44.

Compounding the Field of View—Overview

For a given transducer array 16 there is a given field of view defined by the number of transducer elements and the beamforming parameters for controlling the ultrasound signal transmission and reception. To generate compounded images, image data frames are combined. More specifically, limited field of view image data frames are correlated and registered to define an enlarged 2D or a 3D image. First, echo data is received and beamformed to derive one or more limited field of view frames of image data while the sonographer moves the transducer 16 along the patient's skin surface. Second, correlation of data within 2 or more frames is performed to derive motion vectors for each data element in a given frame. Third, the correlated data is used to define an image. The resulting image is achieved using conventional splicing or rendering techniques and/or by projecting the data into 3D space.

Figures 2, 3:
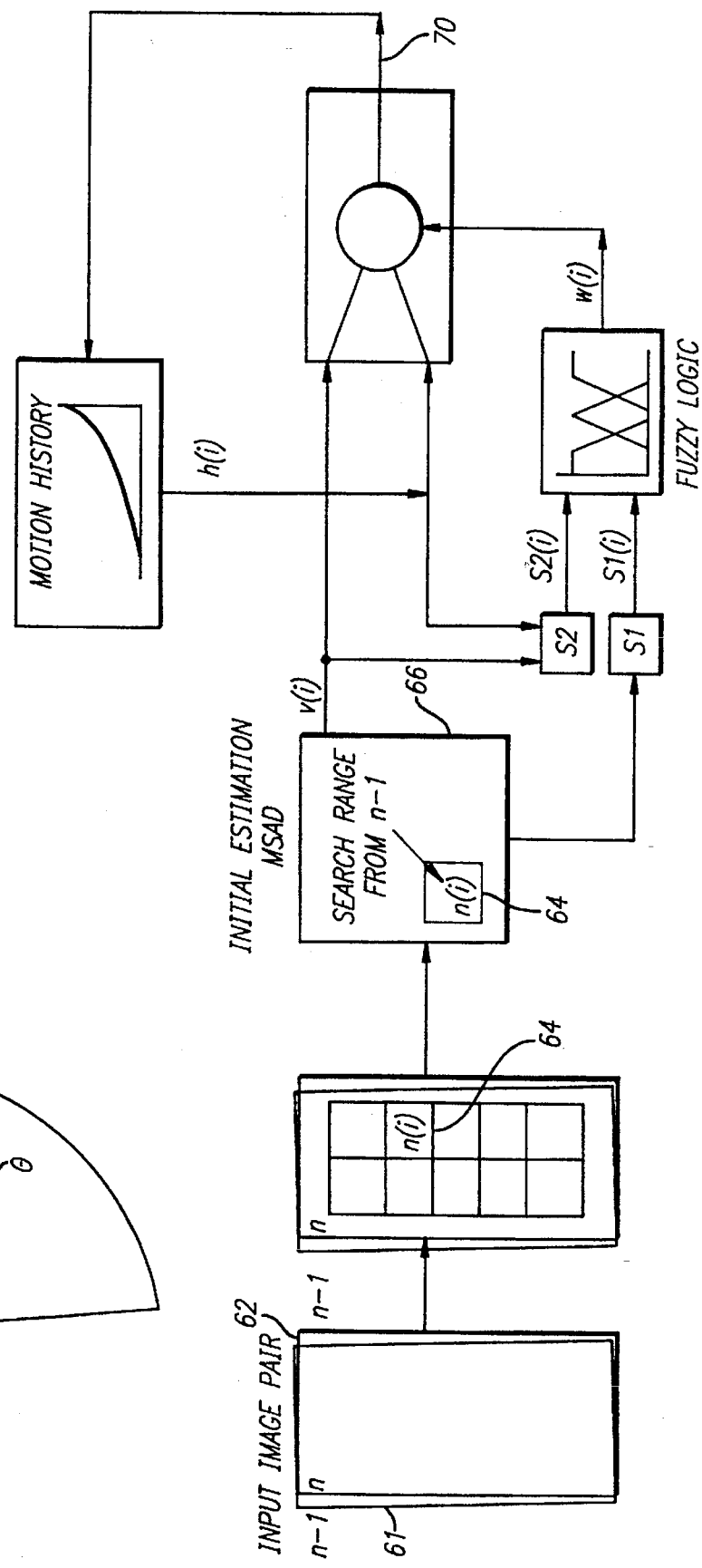
FIG. 2 is a perspective view of the transducer of FIG. 1 along with its scan plane and directional reference axes.
FIG. 3 is a processing block diagram of a method for detecting in-plane transducer motion.

Referring to FIG. 2 the transducer array 16 is shown. The sonographer moves the transducer array 16 within any of six degrees of freedom. The scan plane 40 defined by the unobstructed path of the ultrasound energy emitted from the transducer 16 is used as a reference plane for naming the various degrees of freedom. Translation within the scan plane 40 of the transmitted ultrasound is referred to as being "in-plane". Movement of the transducer in-plane along an azimuthal (e.g., 'x') axis is referred to as lateral translation, or in-plane lateral translation. Movement of the transducer in-plane inward toward the patient (e.g., along a y axis) is referred to as axial translation, or in-plane axial translation. Rotating the transducer (at an angle θ) within the scan plane about a normal axis z, as if adjusting the beam steering, is referred to as in-plane rotation. Movement of the transducer to move the scan plane parallel to its prior position (e.g., along a 'z' axis) is referred to as elevational translation. Movement of the transducer to rotate the scan plane (at an angle α) about the 'y' axis is referred to as axial rotation, Movement of the transducer to rotate the plane (at an angle φ) about the 'x' axis is referred to as rotation about the transducer face.

With regard to the step of correlating the data, data frames are correlated to estimate in-plane motion resulting in two-dimensional motion vectors for each data element of a given frame. Next, an elevational (out-of-plane) motion component is derived, then out-of-plane axial rotation and rotation about the face components are derived. The in-plane and out-of-plane motion vector components define a 3D motion vector for each pixel of an image frame.

Estimating In-Plane Transducer Motion

FIG. 3 shows a block diagram relating to a method for determining in-plane transducer motion. Correlation for in-plane transducer motion is performed for each frame relative to a prior frame. FIG. 3 shows two consecutive image frames 61, 62 denoted as frames n-1 (the previous frame) and frame n (the current frame). The previous image frame n-1 is treated as a reference image frame. The current image frame n is acquired by moving the transducer 16 of FIG. 1 along the skin surface 38.

In one embodiment, the frame n is divided into a plurality of sub-frame blocks 64 to derive frame motion. Local in-plane motion is derived for each block 64. For i total blocks, the i-th block of frame n is referred to as block n(i). Preferably block size is not to be so small as to decorrelate rapidly with relatively large degrees of motion. Further, block size is not to be so large that motion estimation becomes unstable. In a preferred embodiment a block size of 48×48 pixels has been found to be acceptable for motion estimation for a 200×400 pixel image frame.

Local motion of each block n(i) is estimated by moving the block n(i) around on the n-1 image frame to find the best match. In a preferred embodiment a search region 64 on image frame n-1 is selected. Such region 64 is smaller than the total area of image frame n-1. In a preferred embodiment a search region size of 32 pixels in each search direction is used for an input image frame rate of 7.5 frames/second, resulting in a search region 66 size of 64×64 pixels.

In one embodiment the "best match" is determined using a minimum sum-absolute-difference (MSAD) technique to match the n(i) block with a specific search region of the reference frame n-1. The sum-absolute difference is the sum of absolute differences between corresponding pixel values between a given block and a given search region. The search region 64 with the best match to n(i) is the search region where the sum of absolute differences is a minimum. To improve the computation time, various search techniques are sued which reduce the amount of MSAD computations. One technique uses a conventional moving picture expert group ('MPEG') encoder. MPEG encoders are available commercially which perform a rough estimate of MSAD location based on historical movement of an image. A best match is sought between an image characteristic within a block 64 and a search region by searching within a local area including a finite dimensional range (e.g., such as within 10 pixels in x and y directions) relative to the image characteristic. A local 2D motion vector v(i) is assigned to a given block n(i).

Accuracy of the local 2D motion vector v(i) is improved by applying constraints to the imaging process. For example, because motion in the y direction from one frame to the next is usually smaller than in the x direction and because the transducer moves along the patient's contour, transducer motion is characteristically more horizontal (x direction) than vertical (y direction). A fast adaptive coarse/fine MSAD search strategy therefore is devised for reducing the number of computations. Specifically, the implemented search range is larger in the x direction than in the y direction and is adaptive to overall motion history. For example, if motion history is in the +x direction, a coarse search is first performed with an increased search area length in the x direction, followed by a fine search. Such an approach has been found to reduce the number of computations substantially.

Another technique for improving results is to estimate the quality and reliability of the MSAD measurement. Quality of the MSAD measure is determined by calculating a term S1(i) as the difference between an MSAD value for a given block n(i) and a mean SAD value. Reliability is measured by calculating a term S2(i) as the motion vector deviation from a past history h(i). Motion vector history h(i) from a past block is a recursive weighted average of prior motion vector values for a given block n(i). In one embodiment a fuzzy logic control block receives S1(i) and S2(i), then combines them to produce a single output w(i) representing the degree of accuracy of the motion vector v(i). Seven fuzzy logic rules are used in a preferred embodiment as listed below:

(1) If S1(i) is low and S2(i) is low, then w(i) is medium;

(2) If S1(i) is medium and S2(i) is low, then w(i) is high;

(3) If S1(i) is high and S2(i) is low, then w(i) is very high;

(4) If S1(i) is low and S2(i) is medium, then w(i) is low;

(5) If S1(i) is medium and S2(i) is medium, then w(i) is medium;

(6) If S1(i) is high and S2(i) is medium, then w(i) is high;

(7) If S2(i) is high, then w(i) is very low.

Thereafter, a centroid defuzzification technique is used to convert the fuzzy output into a numerical value w(i). With w(i) obtained, the motion vector v(i) estimate is improved. If w(i) is large then v(i) is used directly as the final 2D in-plane motion vector 70. If w(i) is very small, then the average frame motion history h(i) is used as the final 2D in-plane motion vector 70. Otherwise, w(i) is used as a weighting factor to avenge v(i) and h(i). For example, for a w(i)=0.6, the final 2D in-plane motion vector is: 0.6 v(i)+ (1−0.6)h(i).

The method and apparatus for correlating in-plane transducer motion is described in more detail in commonly-assigned U.S. patent application Ser. No. 08/414,978 filed Mar. 31, 1995 of Lee Weng and Arun P. Tirumalai for "Method and Apparatus for Generating Large Compound Ultrasound Image." Such application is incorporated herein by reference and made a part hereof.

Estimating Elevational Transducer Motion

Once an image frame n is correlated for in-plane motion, the data is rotated based upon the final 2-dimensional in-plane motion vector to factor out the in-plane motion variation. The result for a given fame n is an intermediate frame m. The multiple intermediate frames each have in-plane motion factored out. Such intermediate frames now are correlated for out-of-plane motion. According to alternative embodiments, time delay, spectral breadth, power or speckle decorrelation is used as an indicator of elevational translation. Elevational translation variation among transducer elements in the same frame then is used to identify the presence of axial rotation and rotation about the face of the transducer array 16.

Time Delay as an Estimate of Elevational Translation

Time delay is a useful indicator of elevational motion for a 1.5-dimensional ('1.5D') or a 2-dimensional transducer array. A 1.5 D transducer away and a 2D transducer array each have multiple rows of transducer elements. In a 2D transducer array beamforming parameters are controllable for each element in the array. In a 1.5D array steering control along the elevational direction is omitted, focussing along the elevational direction is limited to symmetrical focussing and apodization profile along the elevational direction (e.g., z-axis) is limited to a symmetrical profile. Beams formed by multiple transducer elements occurring in a given transducer array column (i.e., along the elevational z axis) typically overlap. The resulting beams form a variable-sized composite beam element, rather than an independent beam element for each transducer element. However, by examining the echo samples in the near field for such transducer elements before overlap occurs, the data from each transducer element in a given column along the elevational direction is independent. Examining such independent beam elements is useful for estimating time delay.

The received signal (s) from each transducer element (n) in a given column (e.g., x) along the elevation (z) at a fixed depth ($y_0$) over time (t), is referred to as $s(x,y_0,z_n,t)$. As the transducer array moves along the elevation, ultrasound scatterers pass into the scan-plane of a transducer element $z_0$ at a time $t_0$ and beneath an element $z_1$ at a time $t_1$. The measure of the time delay between the signals from each of the two elements, (i.e., $z_0$ and $z_1$) is directly proportional to transducer velocity.

To measure the time delay in-plane motion is factored out. Thus, the intermediate frames are used to measure time delay. Time delay between elements in a given column of elements along the elevation is estimated using any of several alternative criteria. According to a specific embodiment a Sum-Absolute-Difference (SAD) search is performed using equation (1) below:

$$\epsilon_r = \sum_i |s(x, y_0, z_0, t) - s(x, y_0, z_1, t - \tau)| \quad (I)$$

where $t_1 - t_0 = \tau$, the time delay, corresponds to the minimum SAD, $\epsilon_\tau$.

The estimated time delay then is transformed into an elevational motion vector for a given transducer element. An elevational motion vector is derived for each transducer element and assigned to each data item in a given intermediate frame.

Spectral Broadening Estimates

An alternative indicator for elevational motion is the spectral breadth of a pulsed-wave doppler spectrum for a given transducer element. As a given transducer element is translated in the elevation direction (i.e., along the z axis) a single sample is taken periodically at a given range. The sampling rate is defined by a pulse repetition frequency. Each sample is transformed from the time domain into the frequency domain using a fast Fourier transform ('FFT') or the like. The resulting frequency domain representation of multiple samples from the same element is called a pulsed-wave doppler spectrum. The spectrum is determined by transducer element geometry, the pulse repetition frequency and the velocity of the transducer movement For imaging of stationary tissue and movement of the transducer in only one direction (i.e., the elevational direction), increasing transducer velocity compresses the time-domain signal and results in a broader spectrum. Decreasing transducer velocity expands the time-domain signal and results in a narrower spectrum. A stationary transducer corresponds to a delta function at DC frequency. Similar results occur for signals with motion in additional degrees of freedom after correction for such degrees of freedom.

Before measuring spectral breadth, in-plane motion is factored out of the data samples. Thus, data from the intermediate frames is used to derive the spectrum for a given transducer element. At a first step, a series of repeated samples are collected for a single depth over time from the intermediate frames of data samples. At a second step, a fast Fourier transform is derived for the transducer element corresponding to such collected samples. The fast Fourier transform for the sample transducer element is given below where S is the signal spectrum for given transducer element, $z_0$:

$$S(x_0, y_0, z_0, w) = \Sigma s(x_0, y_0, z_0, t) e^{jwt} dt$$

As the spectrum is expected to be triangular, one measure for determining breadth of the spectrum is to fit a triangle to the intermediate frame data, then determine the zero crossovers. The frequency band between zero crossovers are a measure of spectral breadth. Alternatively, a 3 dB width or 6 dB width measurement of the spectrum is used as the measure of spectral breadth.

In one embodiment samples from multiple intermediate frames are used to define a spectrum and derive spectral breadth for a given transducer element $z_0$ of a current intermediate frame m. The spectral breadth then is scaled to define an elevational motion vector for the transducer element $z_0$. The elevational motion vector is assigned to various data items within the current intermediate frame m. The same process then is repeated for each transducer element in the transducer array 16 for each intermediate frame m to achieve elevational motion vectors for each pixel of each intermediate frame.

Power Estimation

Another indicator of elevational translation is derived from the power function of an echo signal received at a given transducer element. The power function of the echo signal is approximately equal to the integral of the pulsed-wave doppler spectrum. More significantly, the power function of the doppler signal is proportional to elevational velocity.

The power function is obtained using a color flow processing method in which the amount of power traversing a wall filter is measured. As a transducer element is moved along the elevational direction, the pulsed-wave doppler spectrum broadens. A low-pass wall filter is applied to the received signal. A broader spectrum output from the wall filter correlates to more energy in the pass band of the filter. The amount of energy correlates directly to the velocity of the transducer. Because axial and lateral translation also appears as increased energy in the pass band, the effects of axial and lateral translation are first factored out before estimated elevational translation using the power mode. More specifically, the intermediate frame data for a given transducer element is passed through the wall filter.

The power mode estimate is given below in equation (II):

$$P = \sqrt{N^2 + D^2} \quad (II)$$

The power function is obtained from the following echo signal equation (III) below received at a given transducer element:

$$D + jN = \sum_i (I_i + jQ_i)(I_{i-1} + jQ_{i-1}) \quad (III)$$

where D+jN is a complex input signal passed through the wall filter.

The change in the power faction over time is directly proportional to the elevational velocity of the given transducer element, The resulting power function is sealed to define velocity. An elevational velocity vector component is derived for each transducer element in the transducer array 16 for each intermediate frame.

Speckle Decorrelation

According to still another technique elevational motion is derived by estimating the rate of speckle decorrelation within successive intermediate flames. As the transducer 16 is moved in the elevational direction, the ultrasonic speckle changes due to changes of the anatomical structure in the scan plane. The elevational velocity is estimated by examining the rate of speckle decorrelation in the echo response data. More specifically, elevational motion is estimated by examining the rate of speckle decorrelation in the echo response data in the intermediate frames.

Speckle decorrelation is performed for multiple subframes of each intermediate frame. Such decorrelation is scaled to define an elevational velocity component. In a specific embodiment an elevational velocity vector component is derived for multiple sub-frames of each intermediate frame using a moving window of four intermediate frames.

Estimating Axial Rotation and Rotation about the Transducer Face

Elevational motion vectors for multiple transducer elements are used to derive other out-of-plane motions. For example, axial rotation is estimated using multiple elevational translation estimates. In one embodiment two estimates of elevational translation are determined at either end of a row of transducer elements (i.e., along the azimuthal x axis). Estimates at different depths then equate to an estimate for axial rotation, Similarly rotation about the face of the transducer is estimated using two estimates of elevational translation taken at either end of a given column of transducer elements (i.e., along the elevational z axis). Estimates at different depths then equate to an estimate for rotation about the face of the transducer 16.

Combining Image Frames

Once local motion vectors are achieved for each pixel of block of an image frame, the vector components are combined to define a global motion vector for a given image data frame, n. In one embodiment a minimum least squares error parameter fitting is used to combine the motion vector outputs, using multiple optimization parameters. The weighting gives a motion vector having a larger weight w(i) more effect than those having a smaller weight. Thus, the more reliable motion vectors contribute more heavily to the optimization process.

The geometrically correlated frames are combined to form a compounded 3D image. Three techniques for combining the corrected frames include, image growing, recursive spatial compounding and ramp rounding. Image growing uses new pixel data in non-overlapping portions of a n image buffer. Recursive spatial compounding recursively averages now image frames with an existing compounded image. Ramp compounding gives weight ramps for both new image frames and an existing compounded image in the overlapping area. The compounded image then is displayed on a video display terminal 28 or other display device, providing a full 3D image.

Meritorious and Advantageous Effects

One advantageous effect of the invention is that by correlating data from various frames to detect various translational and rotational movements of a transducer probe, a dedicated hardware position/motion sensor is avoided. As a result, the transducer probe need not be altered to accommodate the additional sensor.

It should be apparent that the above method and apparatus is applicable to both real-time imaging and regeneration of recorded image information. In application, a physician may use a conventional ultrasound system to produce image flames that are recorded onto a permanent storage medium, such as a tape. Subsequently, the image frames are processed into art extended field of view image for later viewing by a physician by bringing the recorded image frame data to a viewing station. Then viewing station processes the image frame data using the method described herein. It should also be apparent that the method and apparatus of this invention, are not limited to processing of ultrasound images, but are equally applicable to other imaging modalities, such as radar or photographic imaging.

What is claimed is:

1. A method for generating an ultrasound image of a patient target area encompassing a field of view extended beyond a given transducer array's field of view, comprising the steps of:

moving the transducer array within any of six degrees of freedom while the transducer array is positioned at a patient in the vicinity of the target area and while the transducer array emits ultrasound signals and receives returning echoes of the emitted ultrasound signals;

sampling the received echoes within a scan plane at each active transducer element within the transducer array to generate a plurality of frames of echo data for respective positions of the transducer array relative to the patient, a given frame of echo data encompassing a field of view of a first size;

correlating the plurality of frames of echo data to derive at least one in-plane motion vector component for each one of multiple frames of the plurality of frames;.

performing data rotation on said multiple frames to derive corresponding multiple intermediate frames in which in-plane motion variation is factored out;

correlating the multiple intermediate frames to derive at least one out-of-plane motion vector component for each one of the multiple intermediate frames;

aggregating correlated portions of the multiple intermediate frames using the at least one in-plane motion vector component and the at least one out-of-plane motion vector component of each frame to define a 3-dimensional image encompassing a field of view of a second size, the second size larger than the first size.

2. The method of claim 1, in which the step of correlating multiple intermediate frames comprises the step of estimating time delay between the corresponding signals received at each one of at least two transducer elements in an elevational column of transducer element.

3. The method of claim 2 in which time delay is estimated by a minimum signal magnitude difference among a summation of absolute signal magnitude differences.

4. The method of claim 1, in which the step of correlating multiple intermediate frames comprises the step of estimating spectral breadth of a pulsed-wave doppler spectrum derived from a series of repeated echo data samples of multiple intermediate frames at a single depth over time.

5. The method of claim 1, in which the step of correlating multiple intermediate frames comprises the steps of passing data samples from a given transducer element for each frame of the multiple intermediate frames through a low-pass wall filter to derive a filtered sample set, and deriving a power function of the filtered sample set.

6. The method of claim 1, in which the step of correlating multiple intermediate frames comprises the step of estimating rate of speckle decorrelation among the multiple intermediate flames.

7. The method of claim 1, in which the transducer array defines a face of transducer elements, and in which at least one out-of-plane motion vector component comprises an elevational motion component, axial rotation motion component and a rotation-about-the-face motion component.

8. An ultrasound diagnostic imaging system for generating an ultrasound image of a patient target area encompassing a field of view extended beyond a given transducer array's field of view, comprising:

a transducer array having a plurality of transducer elements arranged in a plurality of rows and columns, the transducer array movable within any of six degrees of freedom while positioned at a patient in the vicinity of the target area, the transducer array emitting ultrasound signals and receiving returning echoes of the emitted ultrasound signals;

a receiver which samples the received echoes within a scan plane at each active transducer element within the transducer array to generate a plurality of frames of echo data for respective positions of the transducer array relative to the patient, a given frame of echo data encompassing a field of view of a first size;

processing means for:
  correlating the plurality of frames of echo data to derive at least one in-plane motion vector component for each one of multiple frames of the plurality of frames;
  performing data rotation on said multiple frames to derive corresponding multiple intermediate frames in which in-plane motion variation is factored out;
  correlating the multiple intermediate frames to derive at least one out-of-plane motion vector component for each one of the multiple intermediate frames; and
  aggregating correlated portions of the multiple intermediate frames using the at least one in-plane motion vector component and the at least one out-of-plane motion vector component of each frame to define a 3-dimensional image encompassing a field of view of a second size, the second size larger than the first size; and a display device receiving a video signal corresponding to the 3-dimensional image which displays the 3-dimensional image over a field of view encompassing the second size.

9. The apparatus of claim 8, in which the processor means correlates the multiple intermediate frames by estimating time delay between the corresponding signals received at each one of at least two transducer elements in a transducer array column.

10. The apparatus of claim 9 in which time delay is estimated by a minimum signal magnitude difference among a summation of absolute signal magnitude differences.

11. The apparatus of claim 8, in which the processor means correlates multiple intermediate frames by estimating spectral breadth of a pulsed-wave doppler spectrum derived from a series of repeated echo data samples of multiple intermediate frames at a single depth over time.

12. The apparatus of claim 8, further comprising a low pass wall filter and wherein data samples from a given transducer element for each frame of the multiple intermediate frames pass through the low-pass wall filter to derive a filtered sample set; and in which the processor means correlates multiple intermediate frames by deriving a power function of the filtered sample set.

13. The apparatus of claim 8, in which the processor means correlates multiple intermediate frames by estimating rate of speckle decorrelation among the multiple intermediate frames.

14. The apparatus of claim 8, in which the transducer array defines a face of transducer elements, and in which at least one out-of-plane motion vector component comprises an elevational motion component, axial rotation motion component and a rotation-about-the-face motion component.

* * * * *